(12) United States Patent
Christensen et al.

(10) Patent No.: US 7,384,745 B2
(45) Date of Patent: Jun. 10, 2008

(54) **NUCLEIC ACID SEQUENCES FOUND IN *DROSOPHILA MELANOGASTER* THAT ENCODE PROTEINS ESSENTIAL FOR VIABILITY AND METHOD OF USE**

(75) Inventors: Alan C. Christensen, Lincoln, NE (US); Douglas R. Dorer, West Davenport, NY (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 463 days.

(21) Appl. No.: 10/842,130

(22) Filed: May 10, 2004

(65) Prior Publication Data
US 2005/0202401 A1    Sep. 15, 2005

Related U.S. Application Data

(60) Provisional application No. 60/468,890, filed on May 8, 2003.

(51) Int. Cl.
*C12Q 1/68* (2006.01)

(52) U.S. Cl. .......................................... 435/6; 536/23.5

(58) Field of Classification Search ...................... None
See application file for complete search history.

(56) References Cited

U.S. PATENT DOCUMENTS

| 6,468,770 B1 | 10/2002 | Keyes et al. |
| 2002/0160934 A1 | 10/2002 | Broadus et al. |

FOREIGN PATENT DOCUMENTS

| WO | WO02057455 | 7/2002 |
| WO | WO02077157 | 10/2002 |

OTHER PUBLICATIONS

Denell, "The genetic analysis of a uniquely dose-sensitive chromosomal region of *Drosophila melanogaster.* " Genetics. Oct. 1976;84(2):193-210.

Dorer and Christensen, "The unusual spectrum of mutations induced by hybrid dysgenesis at the *Triplo-lethal* locus of *Drosophila melanogaster.*" Genetics. Aug. 1990;125(4):795-801.

Dorer et al., "A family of genes clustered at the *Triplo-lethal* locus of *Drosophila melanogaster* has an unusual evolutionary history and significant synteny with *Anopheles gambiae.*" Genetics. Oct. 2003;165(2):613-21.

Dorer et al., "Suppression of a lethal trisomic phenotype in *Drosophila melanogaster* by increased dosage of an unlinked locus." Genetics. May 1993;134(1):243-9.

Dorer et al., "The *Triplo-lethal* locus of *Drosophila*: reexamination of mutants and discovery of a second-site suppressor." Genetics. Nov. 1995;141(3):1037-42.

Eissenberg et al., "dELL, an Essential RNA Polymerase II Elongation Factor with a General Role in Development." Proc Natl Acad Sci U S A. Jul. 23, 2002;99(15):9894-9.

Keppy and Denell, "A mutational analysis of the *triplo-lethal* region of *Drosophila melanogaster.*" Genetics. Mar. 1979;91(3):421-41.

Krebs et al., "Use of subtracted libraries and macroarray to isolate developmentally specific genes from the mosquito, *Aedes aegypti.*" Insect Biochem Mol Biol. Dec. 2002;32(12):1757-67.

Lindsley et al., "Segmental aneuploidy and the genetic gross structure of the *Drosophila* genome." Genetics. May 1972;71(1):157-84.

Roehrdanz and Lucchesi, "Mutational events in the *triplo-* and *haplo-lethal* region (83DB) of the *Drosophila melanogaster* genome." Genetics. Jun. 1980;95(2): 355-366.

Smoyer et al., "Phenotype of the *Triplo-lethal* locus of *Drosophila melanogaster* and its suppression by hyperoxia." Genet Res. Dec. 2003;82(3):163-70.

*Primary Examiner*—James S Ketter
(74) *Attorney, Agent, or Firm*—Thompson Coburn LLP; Charles P. Romano (57) ABSTRACT

Within the unique Triplo-lethal region (Tpl) of the *Drosophila melanogaster* genome we have found a cluster of 20 genes encoding a novel family of proteins. This family is also present in the *Anopheles gambiae* genome and displays remarkable synteny and sequence conservation with the *Drosophila* cluster. The family is also present in the sequenced genome of *Drosophila pseudoobscura*, and homologs have been found in *Aedes aegyptii* mosquitoes and the honeybee (*Apis mellifera*), but it is not present in the sequenced genome of any non-insect species. Phylogenetic analysis suggests that the cluster evolved prior to the divergence of *Drosophila* and *Anopheles* (250MYA) and has been highly conserved since. The ratio of synonymous to non-synonymous substitutions and the high codon bias suggest that there has been selection on this family both for expression level and function. We suggest that this gene family is Tpl, name it the Osiris family, and suggest possible functions. We also suggest that this family of proteins, due to the unique dosage sensitivity, and the lack of homologs in non-insect species, would be a good target for genetic engineering or novel insecticides. The proteins also present an excellent means to test compounds for use as possible insecticides.

9 Claims, 11 Drawing Sheets

TABLE 1

Osiris Cluster Sequences with accession numbers and locus tags. The specific sequences may be found by accessing the FlyBase Database of the Drosophila Genome on the World Wide Web at the internet website http://flybase.bio.indiana.edu/, (the specific sequences are most easily accessed by performing a search for a GENE by Protein Name such as Osiris 1, Osiris 2, etc...) or by accessing Genbank at http://www.ncbi.nlm.nih.gov/entrez/query.fcgi with the accession number and locus tag information provided here.

| Protein | Accession # | Locus tag |
|---------|-------------|-----------|
| Osiris1 | AE003600 | CG15585 |
| Osiris2 | AE003600 | CG1148 |
| Osiris3 | AE003600 | CG1150 |
| Osiris4 | AE003600 | CG10303 |
| Osiris5 | AE003600 | CG15590 |
| Osiris6 | AE003600 | CG1151 |
| Osiris7 | AE003600 | CG1153 |
| Osiris8 | AE003600 | CG15591 |
| Osiris9 | AE003600 | CG15592 |
| Osiris10 | AE003600 | CG15593 |
| Osiris11 | AE003600 | CG15596 |
| Osiris12 | AE003600 | CG1154 |
| Osiris13 | AE003600 | CG15595 |
| Osiris14 | AE003600 | CG1155 |
| Osiris15 | AE003600 | CG1157 |
| Osiris16 | AE003600 | CG31561 |
| Osiris17 | AE003600 | CG15598 |
| Osiris18 | AE003600 | CG1169 |
| Osiris19 | AE003675 | CG15189 |
| Osiris20 | AE003675 | CG15188 |
| Osiris21 | AE003631 | CG14925 |
| Osiris22 | AE003699 | CG8644 |
| Osiris23 | AE003774 | CG15538 |

NUCLEIC ACID SEQUENCES FOUND IN *DROSOPHILA MELANOGASTER* THAT ENCODE PROTEINS ESSENTIAL FOR VIABILITY AND METHOD OF USE

This application is a non-provisional application which claims priority from U.S. Provisional Patent Application Ser. No. 60/468,890 filed on May 8, 2003 and hereby incorporated by reference in its entirety.

TECHNICAL FIELD

The present invention relates to the fields of biotechnology and genetics, specifically to a cluster of nucleic acid sequences identified in the *Drosophila melanogaster* genome that are critical to the viability of the organism, are highly conserved, have unique sensitivity, and lack homologues in non-insect species. The invention particularly relates to the use of these nucleic acid sequences as effective targets for insecticides based on these features.

BACKGROUND OF THE INVENTION

Insect-borne diseases are a huge and growing problem in world health. The most serious of these is malaria, which affects over 300 million people each year, and kills over one million people. Although the mortality occurs among young children in sub-Saharan Africa, malaria still poses a health risk in the United States, with approximately 3000 cases being reported in 2000-2001 alone.

An important part of a multifaceted approach to this problem is control of the insects that act as vectors for the transmission of disease. A primary means of limiting insect vectors is limiting the number of insects in the population through the use of insecticides. There are two large concerns with regard to the use of insecticides. One is the ability of insects to evolve a resistance to insecticides, which happens frequently. The other concern relates to the general safety and efficacy of the use of insecticides, specifically, some insecticides such as the group of insecticide compounds known as the organophosphates, affect vertebrate nervous systems, and therefore pose a risk to human and animal populations. Therefore, tools that help in the discovery of insecticides that have a broad-spectrum effect on insects across species and yet remain harmless to humans and other animals are very useful in this technical field.

An excellent model for the testing of genetic insecticide targets is *Drosophila melanogaster*. The *Drosophila* genome has been entirely sequenced and it is one of, if not the, most well studied and documented insects in the world. A wide array of genetic and molecular research methods and tools are available for efficacious use with *Drosophila*. In addition, many *Drosophila* genes and proteins are highly conserved across insect species, meaning that research on *Drosophila* genes and proteins will likely have an impact on other insect species as well.

When the *Drosophila* genome was surveyed for dosage sensitive regions only one was found which was both triplo-lethal and haplo-lethal. This locus, located in cytological region 83D4,5-E1,2, was called the Triplo-lethal locus, abbreviated Tpl. Stocks carrying a duplication of Tpl on one homolog and a deficiency on the other homolog are viable, and provide a powerful selection for either up or down mutations when crossed to a wild type fly. Using this selection, Keppy and Denell were able to obtain duplications and deficiencies of Tpl, but were unable to isolate point mutations following EMS or formaldehyde mutagenesis. Roehrdanz and Lucchesi were also unable to isolate point mutations of Tpl following EMS mutagenesis, although they did isolate mutations in the Suppressor of Tpl locus, which has been shown to encode the Ell protein, a general transcription elongation factor.

Three hypotheses have been proposed to explain the lack of point mutations at Tpl: 1) the locus is very small so the mutation rate is very low, 2) the locus does not encode a protein so it is less sensitive to single base changes, and 3) the locus consists of a cluster of genes with at least partial redundancy, such that mutating one of the genes does not rescue the lethality caused by a duplication of the entire cluster. The small size hypothesis predicts that as the number of mutagenized chromosomes increases, eventually mutants will be found. However, we have subsequently screened more than $10^6$ chromosomes and still have not isolated point mutants. The non-protein-coding hypothesis predicts that transposon insertions would inactivate the locus, as would inversions with a breakpoint in the gene, and in spite of considerable effort we have never isolated a P element insertional mutation in Tpl. Thus the most likely hypothesis is that Tpl consists of a cluster of genes with at least partial redundancy.

The complete genomic sequence of *D. melanogaster* has allowed us to test the prediction that the Triplo-lethal region contains a cluster of genes with high similarity. To do that, first we defined the molecular limits of Tpl by isolating and mapping duplications and deletions and then examining the sequence within those limits for repeated genetic units. We describe here the discovery of a multi-gene family in the Triplo-lethal region, consistent with the best hypothesis based on the genetic data. The proteins encoded by this family are novel, although the protein sequences have features that allow us to make predictions about their function. We would expect that a family of genes whose dosage is so critical would be well conserved, and would show evidence for strong selection on expression levels. Comparison of the *Drosophila melanogaster* gene family with the orthologous genes in *Anopheles gambiae* allows us to analyse the expression, selection and evolution of the family.

SUMMARY OF THE INVENTION

It is an object of the present invention to disclose novel, highly conserved genes in insects that can be targeted by insecticides.

Accordingly, the present invention provides for genetic sequences and resulting proteins from *Drosophila melanogaster* that, when over expressed or under expressed, are lethal to an insect.

Another object of the present invention is to provide for a method to test compounds for insecticidal use based on the ability of the compound to inhibit the expression of certain genetic sequences and resulting proteins of an insect that are critical to the viability of the insect.

Yet another object of the present invention is to provide for a method to kill insects by contacting said insect with a compound capable of inhibiting the expression of certain genetic sequences and resulting proteins that are critical to the viability of the insect.

It is yet another object of the present invention to provide for a method to genetically alter an insect to carry a genotype such that, when said insect mates, the progeny of such mating will over express or under express certain genetic sequences, amino acid sequences and resulting proteins critical to the viability of the progeny, and as a result, said progeny will die.

Additional objects, advantages and novel features of the present invention will be set forth in part in the description which follows, and in part will become apparent to those skilled in the art upon examination of the following, or may be learned from practice of the invention.

DESCRIPTION OF THE DRAWINGS

In the accompanying drawings which form a part of this specification and are to be read in conjunction therewith and in which like reference numerals are used to indicate like parts in the various views:

FIG. 1 is an alignment of the amino acid structures of the 18 members of the Osiris gene family (SEQ ID NOS 24-41, respectively in order of appearance).

FIG. 1A is a continuation of FIG. 1

Table 1 is a table listing the 23 different sequences (SEQ ID NOS 1-23, respectively in order of appearance) for the Osiris gene family with accession numbers and locus tag information to allow access to the specific sequences.

DESCRIPTION OF THE INVENTION

*Drosophila* rearrangements and mapping: *Drosophila* stocks were previously described (DORER and CHRISTENSEN 1990; DORER et al. 1995), or were obtained from the Indiana University *Drosophila* Stock Center. Duplications and deficiencies of Tpl were generated by crossing flies carrying both a Δ2-3 source of transposase and a single P element inserted near Tpl to $Y^S X.Y^L$, In(1)EN y;Dp(3;3)Tpl $p^P$/Df(3R)Tpl10 $p^P$. Survivors were backcrossed to the Dp/Df line to establish a stock carrying the new rearrangement, often flanked by the starting P element. Three single P element insertions were used: P{ry$^{+t7.2}$=PZ}l(3)01086$^{01086}$, inserted in RM62, P{hsneo} l(3)neo33$^1$, inserted in castor (COOLEY et al. 1988), and RS2/24, inserted in pollux (VINCENT et al. 1990). Inverse PCR was used to amplify the DNA flanking P-induced rearrangements as described (SPRADLING et al. 1999). DNA sequencing was done by the University of Nebraska DNA Sequencing Facility. Breakpoints were mapped by comparing these sequences to the *Drosophila* genome using BLAST (ALTSCHUL et al. 1997).

Bioinformatics: Sequence similarity searches were done using the BLAST server at http://www.ncbi.nlm.nih.gov, or Vector NTI from Informax. Targeting predictions were done using TargetP 1.01. Transmembrane helix predictions were done with TMHMM 2.0. Multiple alignments based on amino acid sequences were generated by MULTICLUSTAL and ClustalW. Based on this alignment, amino acid distances were estimated by the JTT method. Phylogenetic relationships were reconstructed by using the neighbor-joining (NJ) method. Bootstrap supporting values were estimated from one thousand bootstrap sampling. JTT distance estimation, NJ tree reconstruction, and bootstrap analysis were conducted by Phylip 3.6a3. Codon usage bias was measured as the "effective number of codons" (ENC) developed by Wright. Numbers of synonymous and nonsynonymous substitutions per site were estimated by the Li method. General statistical analyses were conducted with JMP 5 (SAS Institute, Inc.)

Results

Molecular mapping of Tpl: Because we and others have been unable to isolate point or transposon insertion mutations in Tpl, in spite of a very powerfull selection, we took the approach of generating duplications and deletions flanking single P-element insertions. Because the proximal breakpoint of Dp(3;3)Tpl is just distal to the Rm62 gene, we chose three single P-element insertions near Rm62 as starting points for new duplications and deficiencies. Of the 24 duplications and 43 deficiencies that resulted, we were able to accurately map 29 of them by Inverse PCR and sequencing. The smallest duplication, Dp(3;3)Tpl$^{JE10B}$, is duplicated from Rm62 through Pak, a region of approximately 334 kb. The smallest deficiency, Df(3R)Tpl$^{6F}$, also has its distal breakpoint in Pak, confirming that Tpl is located between Rm62 and Pak.

Prior examination of this region in the *Drosophila* genome revealed a previously undescribed family of genes which explains the unusual genetics of Tpl. This family of genes is located in the 168kb region from CG15585 through CG15188, which represents roughly half of the Tpl region defined by the breakpoints. Only 7 of the 27 genes in this region are not members of this family (CG31562, NPFR1, CG15589, CG15597, CG15594, CG31556 and CG31560). BLASTP and PSI-BLAST searching has revealed only three members of the family outside of this cluster (see below). Of these 23 family members, 18 are shown aligned in FIG. 1. The others are described separately below. The complete alignment is given in Supplemental Data. All of the proteins appear to have endoplasmic reticulum signal peptides. In addition to the signal peptide, these proteins have three conserved domains. The first is near the amino terminus and consists of a pair of cysteines usually separated by 7-9 amino acids. The second is a region consisting of four blocks of hydrophobic amino acids, separated by lysines. A proline is usually present in the first two hydrophobic blocks. This region is predicted to be a transmembrane domain and resembles a stop-transfer anchor, thus these are Type I transmembrane proteins with the N-terminus outside the cell and the C-terminus inside. The third domain is a region rich in conserved histidines and tyrosines, including the highly conserved sequence AQXLAY (SEQ ID NO: 87) near the carboxy terminus. A number of different endocytic signaling motifs include tyrosines and copies of one such signal, YXXO, are boxed in FIG. 1. Because the Isis locus partially rescues the effect of trisomy for this region, we call this family of proteins the Osiris family.

Four genes from the cluster at 83E also appear to be members of the Osiris family but cannot be aligned as well and were not shown in FIG. 1, but are aligned In Supplemental Data. These four genes are CG15595, CG15593, CG157 and CG15598. All four of them include the putative transmembrane domain and the conserved tyrosine motif, however CGl15593appears to be internally repeated, and CG1157 and CG15595 are diverged at the ends, perhaps because of errors in predicting the exons CG15598 includes copies of the cysteine motif at both the amino and carboxyl termini, and is predicted to be mitochondrial. In spite of the differences, these four genes are recognizably members of the family, and annotation errors may account for the differences. Through BLAST and PSI-BLAST queries of the NCBI database, we have identified three other members of this family, encoded at three different sites elsewhere in the genome. CG14925(polytene region 32E) and CG15538 (99F) appear to be typical members of the family, and are shown in the alignment in FIG. 1. CG8644(87E) lacks the N-terminal cysteines, though it is otherwise very similar to the others. None of these loci are triplo-lethal or located within haplo-insufficient regions.

Figure 2:
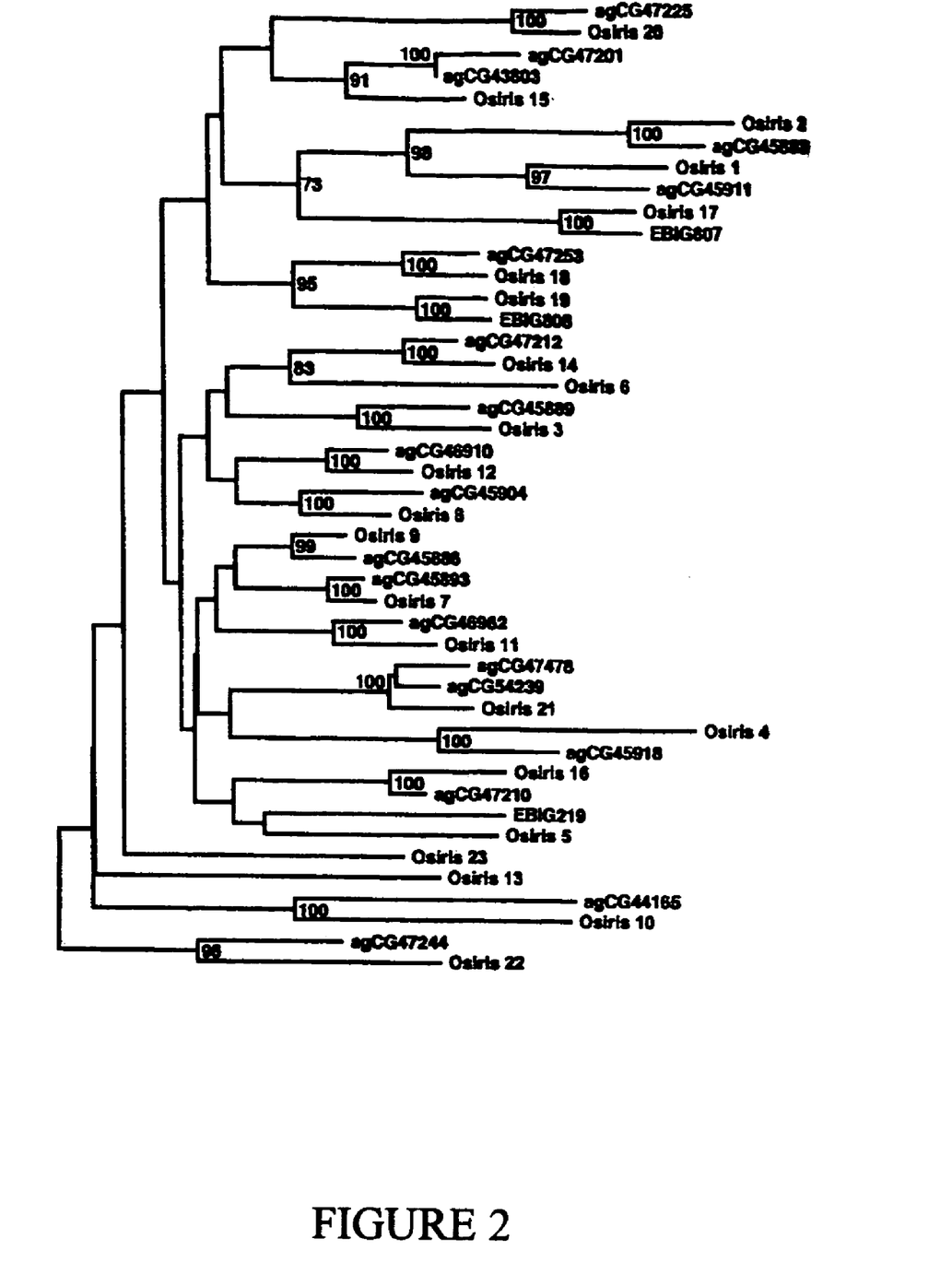
FIG. 2 is a graph of neighbor-joining phylogeny based on the 23 *D. melanogaster* and 22 *A. gambiae* Osiris family genes.

The Osiris gene family is highly conserved between *Drosophila* and *Anopheles*: We compared the genes in this region to the *Anopheles gambiae* genomic sequence, and found that *Anopheles* has an orthologous family of proteins, mostly encoded in two clusters on chromosome 2R. Phylogenetic relationships of the Osiris genes from both species were determined as described in Methods, and the resulting tree is shown in FIG. 2. With very few exceptions the closest relative of each gene is its ortholog in the other species, rather than any of the paralogs in the same species. These orthologous pairs were also supported with high bootstrap values (>90%). This suggests that the family diverged by gene duplication before the divergence of *Drosophila* and *Anopheles*, but that each member of the family has retained its unique features since then. To understand the close relationships between orthologs, we examined the codon usage biases of the genes and the base substitution patterns between orthologous pairs. Codon usage bias was measured as the "effective number of codons" or ENC. It can range from 20 (where only one codon is used for each of the 20 amino acids, and thus codon usage is most biased) to 61 (where all possible codons are used, and there is no bias). The average ENC for more than 12,000 genes from *D. melanogaster* is 49, with a range from 28 to 61. It has been shown that highly expressed genes have high codon usage bias as seen by a low ENC. For example, the average ENC among ribosomal protein genes is 39. The average ENC from the 23 Osiris genes from *D. melanogaster* is 45.1 with a range from 31 to 61. The ENC from the 22 *A. gambiae* homologs range between 33 and 57 with an average of 40.6. The codon usage bias was significantly correlated between orthologous pairs of genes (R=0.52, P=0.02). The average G+C contents at the four-fold degenerate positions are 71% (*D. melanogaster*) and 74% (*A. gambiae*); also significantly correlated between orthologous pairs (R=0.54, P=0.01). On the other hand, both species have low and uncorrelated G+C content in introns (33% for *D. melanogaster* and 43% for *A. gambiae*; R=0.12, P>>0.05). These observations indicate that there is strong selection on these genes and on maintaining the expression levels.

Figure 3:
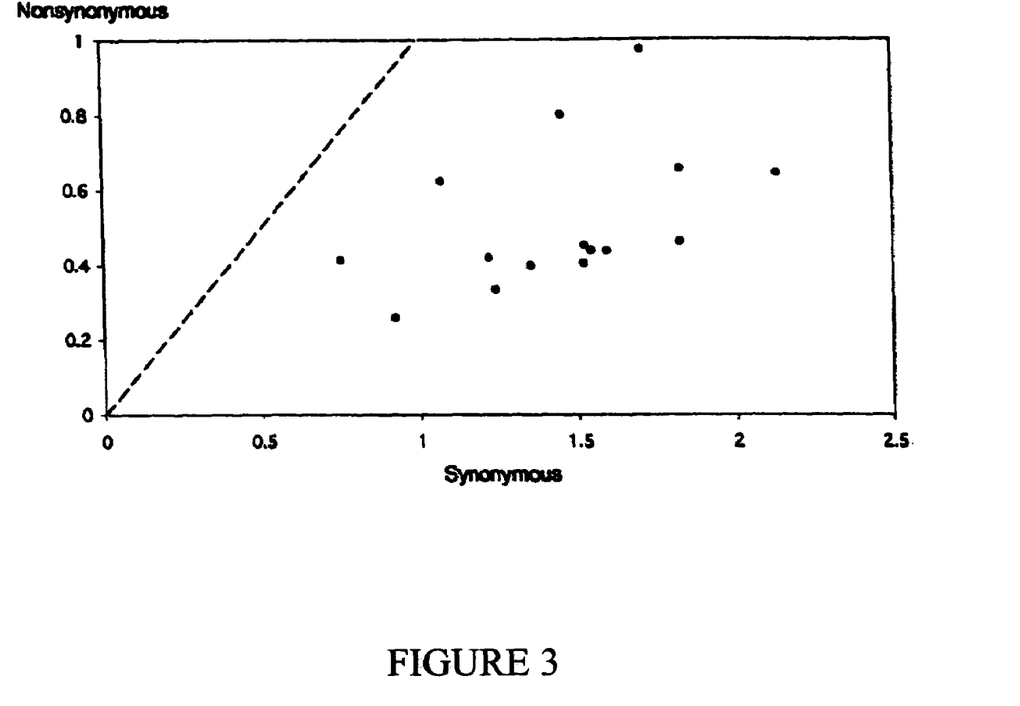
FIG. 3 is a graph showing the number of synonymous and non-synonymous substitutions per site.

A significant negative correlation is observed between the numbers of synonymous substitutions per site and the codon usage bias of orthologous pairs (R=0.76, P=0.002). This again implies that these genes are under translational selection. The average ratio between the numbers of synonymous and nonsynonymous substitutions per site is 0.37, and range from 0.25 to 0.58. These ratios are less than 1.0 (see FIG. 3), indicating that all these genes are under selection. Not surprisingly, these ratios are higher than those obtained within the *Drosophila* lineage. Bergman et al, for example, reported that approximately 90% of such ratios obtained from the comparisons between three *Drosophila* species are under 0.2. Interestingly, nonsynonymous substitution rates are correlated with synonymous substitution rates (FIG. 3; Spearman Rho=0.6, P=0.02). Such correlations have been described in *Drosophila* and mammalian genes. In the case of *Drosophila* genes, translational selection both on codon usage bias and on amino acid substitutions is considered to cause such correlations.

Figure 4:
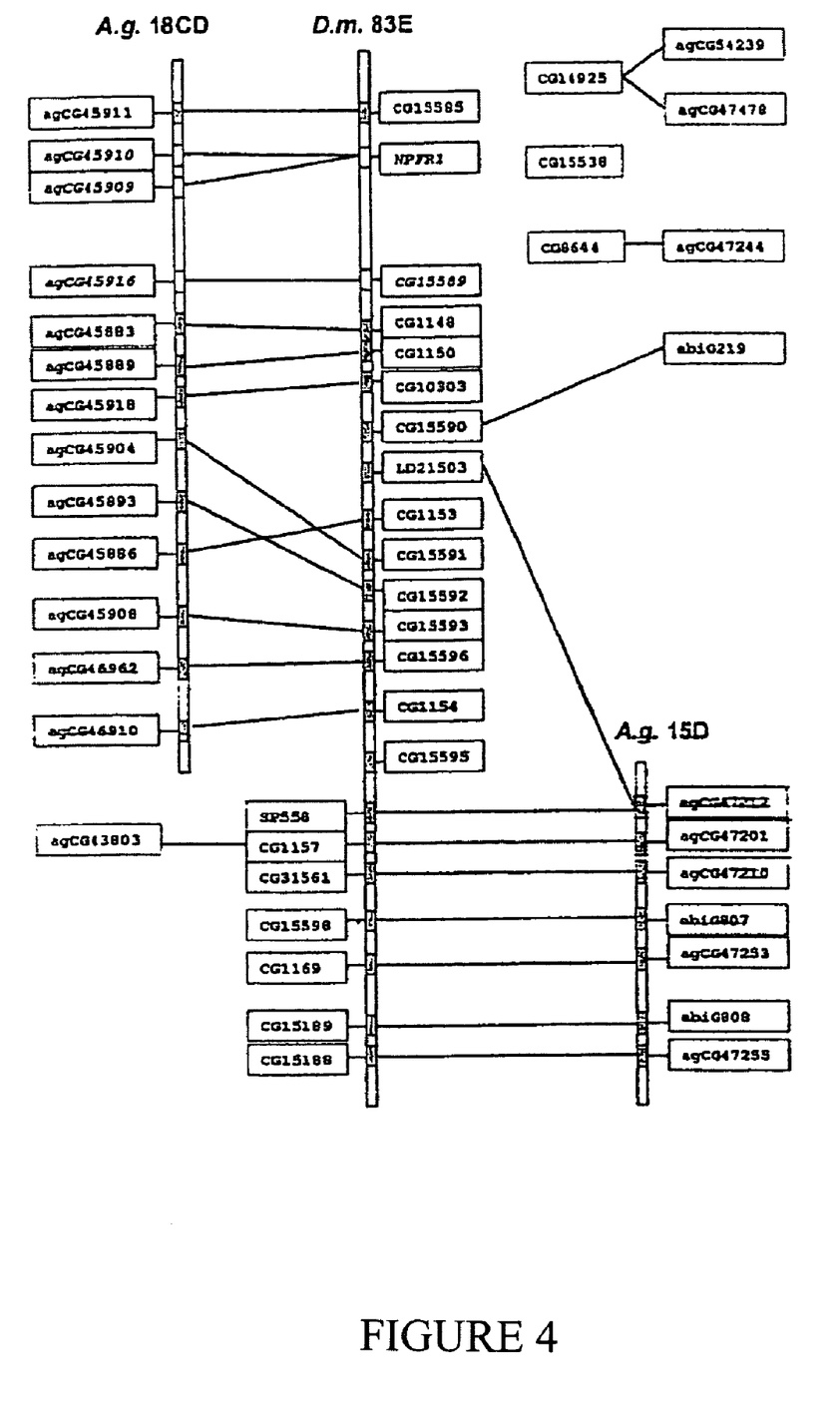
FIG. 4 is a map of the Osiris genes in *D. melanogaster* and *A. gambiae*.

The Osiris gene cluster displays significant synteny:The map locations of most of the *A. gambiae* orthologs are known, and the families maintain a remarkable degree of synteny in the two species. The genes found in the Tpl cluster in *D. melanogaster* are found in the same order in *A. gambiae* in two clusters on chromosome 2. Ten of the family members are in polytene region 18CD, and another seven are in 15D. A comparison of the *Drosophila* and *Anopheles* clusters is shown in FIG. 4. The block of genes from CG15585 through CG1154) retains one of the largest regions of microsynteny found in a comparison of the two genomes. In this interval, nine of eleven pairs of orthologous Osiris genes are in the same order. With only two exceptions in each species the genes are all transcribed from the same strand. This synteny also includes the non-family members NPFR1 and CG15589/agCG45916. Similarly, the block from SP558-CG1155 to CG15188 contains seven family members in the same order as their *Anopheles* orthologs in 15D. CG15595 does not appear to have an *Anopheles* ortholog, and it is located where the family is separated into two clusters in *Anopheles*. Interestingly, its two neighbors, the non-Osiris genes CG15594 and CG15597, also do not have orthologs in *Anopheles*. One hypothesis is that the ancestral species had the genes in one cluster and a rearrangement in the lineage leading to *Anopheles* split it in two, with a loss of these three genes at the breakpoint. Two of the unlinked *Drosophila* family members (CG 14925 and CG8644) have *Anopheles* orthologs that are also unlinked to the main clusters. The other unlinked *Drosophila* family member, CG15538, does not have a clear ortholog.

Figure 5A:
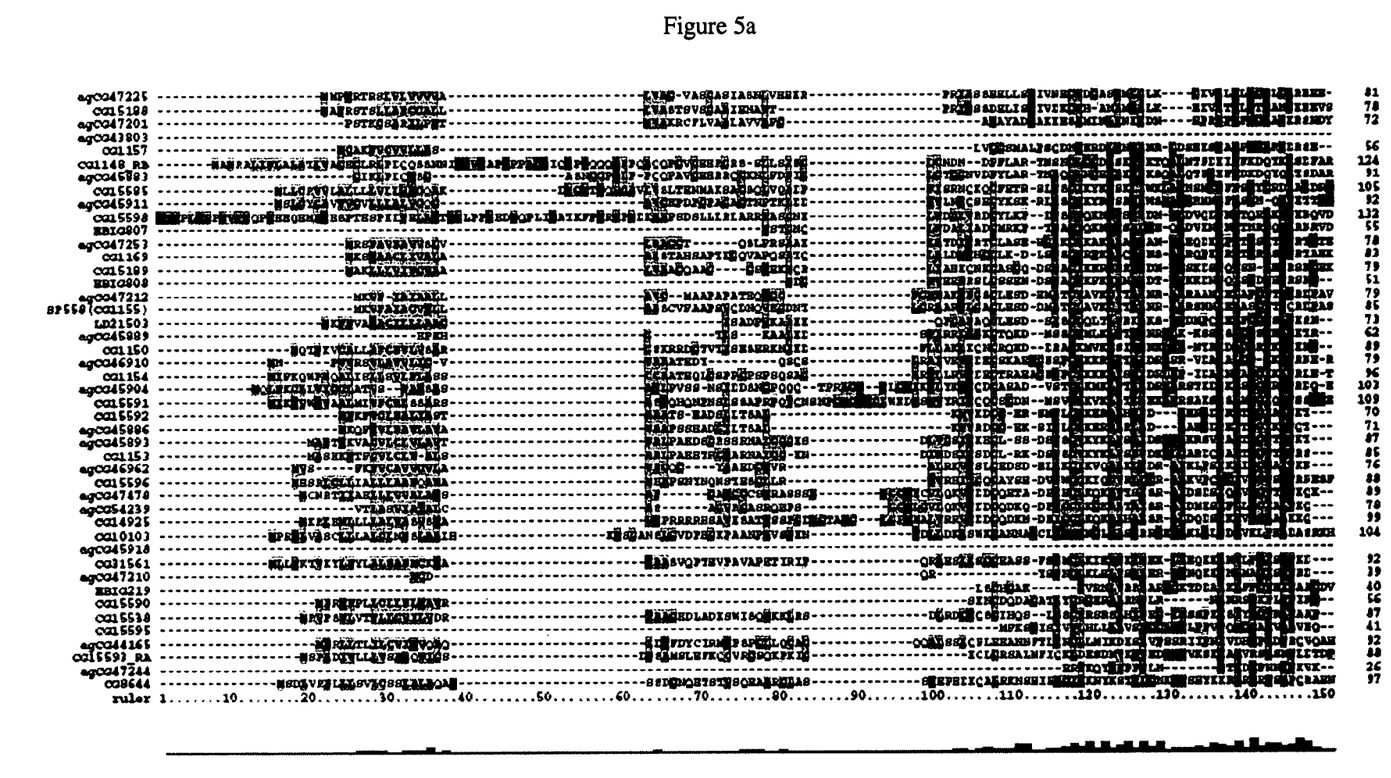
FIG. 5a is a detailed alignment of the amino acid structures of the Osiris gene family (SEQ ID NOS 42-86, respectively in order of appearance).
Figure 5B:
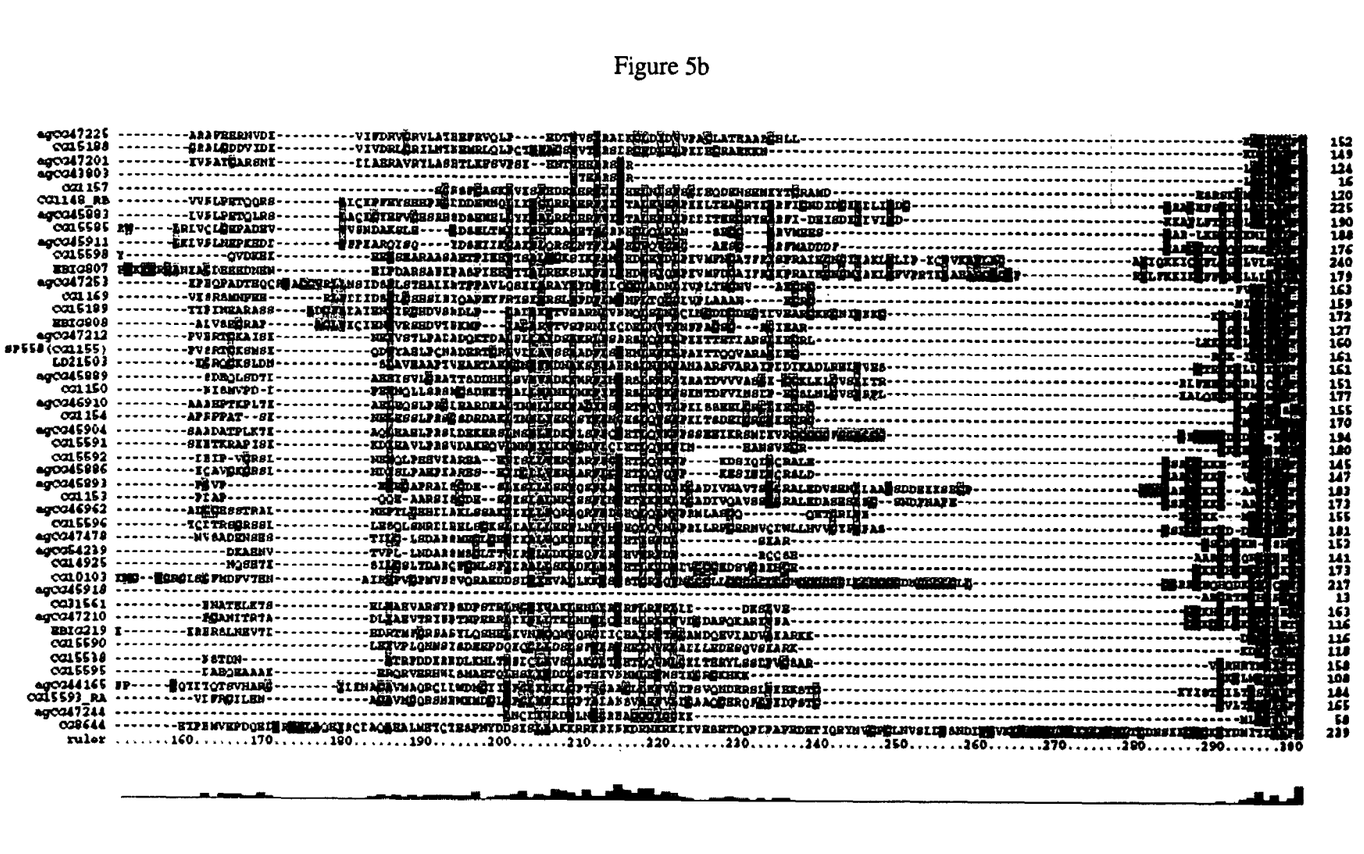
FIG. 5b is a continuation of FIG. 5A.
Figure 5C:
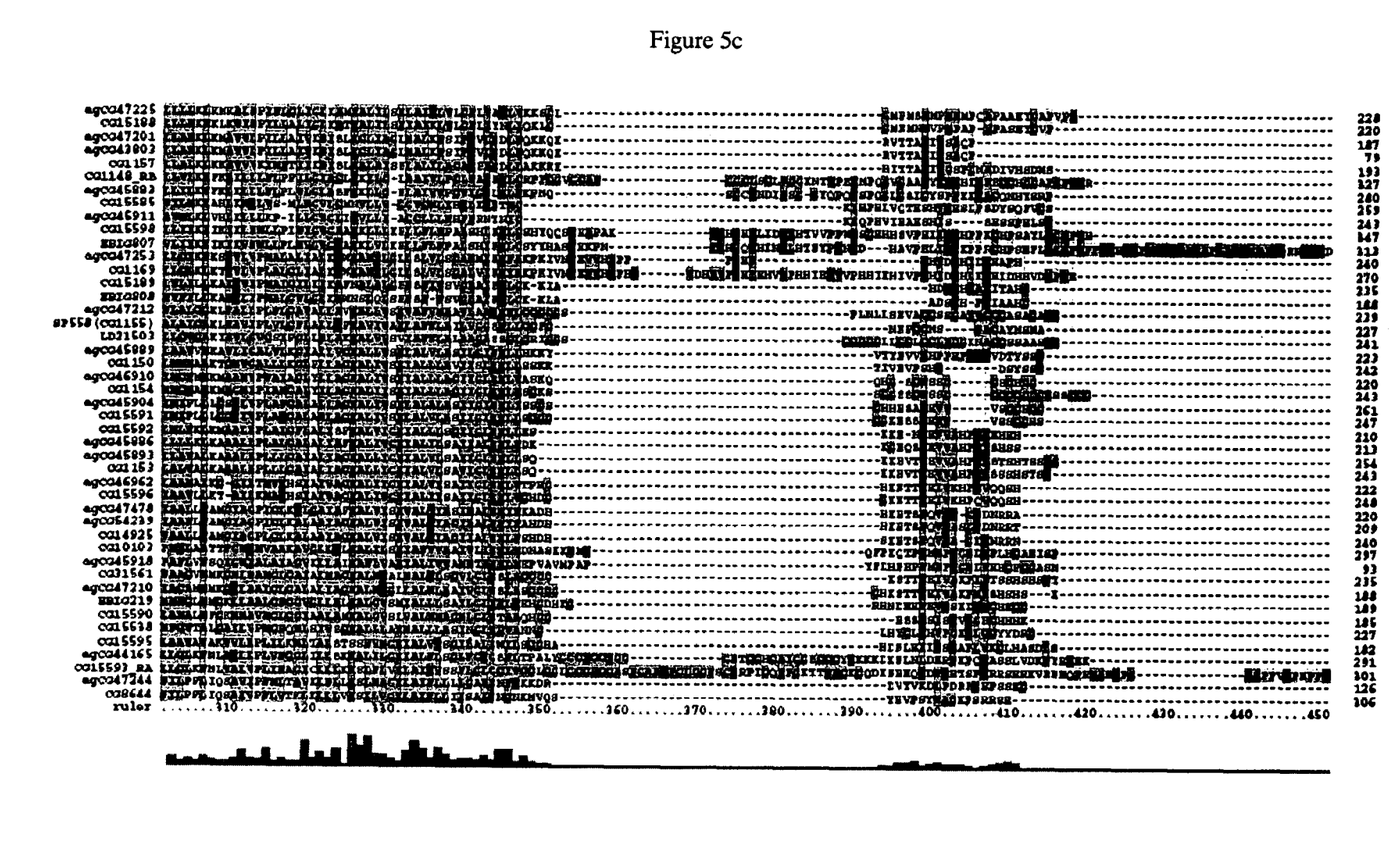
FIG. 5c is a continuation of FIG. 5B.
Figure 5D:
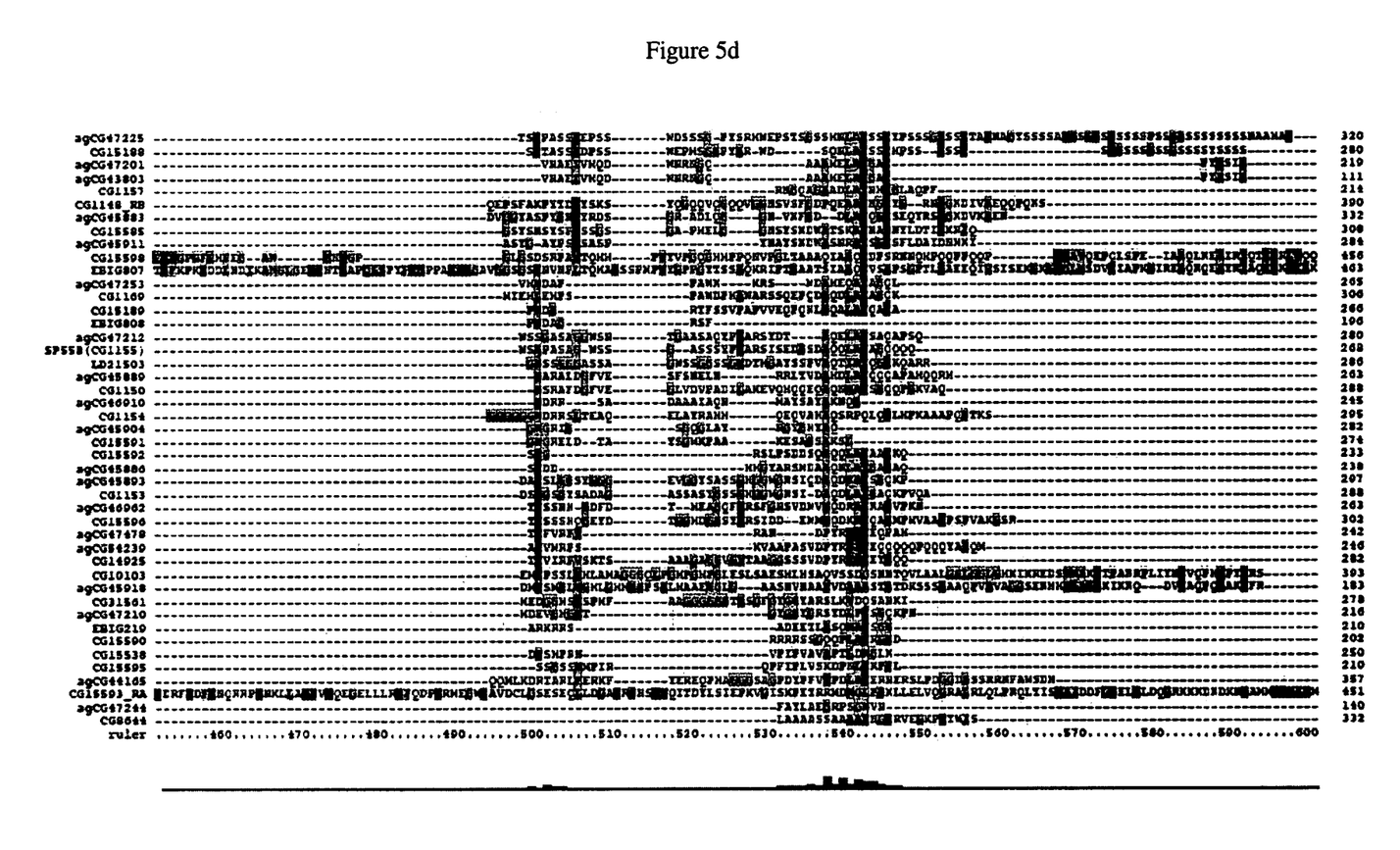
FIG. 5d is a continuation of FIG. 5C.

Osiris family members in other species: Homologs to the Osiris genes have been sequenced in *Drosophila pseudoobscura, Aedes aegypti*, and *Apis mellifera*. Not surprisingly, all 23 family members are found in the *D. pseudoobscura* genome, completely syntenic with the *D. melanogaster* genes (http://hgsc.bcm.tmc.edu/*Dosophila*). Currently, no other insect genomes have been reported to be completely sequenced. However, a partial cDNA from *Aedes aegypti* (GenBank accession BQ789636) encodes a homolog of CG15596. The cDNA sequence contains the putative transmembrane domain, and the high degree of conservation of this region is shown in FIG. 5*a*. A sequence included in the currently available EST data on the honeybee, *Apis mellifera* (GenBank accession numbers B1512836, B15793, and B1509951), has significant homology to the Osiris gene SP558. The incomplete sequence of the honeybee protein contains the signal peptide, the paired cysteines, and the transmembrane domain (FIG. 5*b*). In contrast to the conservation demonstrated in these insect species, no homologs have been sequenced in any other phyla to date. This suggests that whatever function the Osiris proteins are carrying out may be insect or Arthropod specific.

Expression:The lethal phase of Tpl aneuploids is late embryonic or early larval, with the first tissues to be affected being the tracheae and gut. Expression data are available from the Berkeley *Drosophila* Genome Project for some of the Osiris genes (http://www.fruitfly.org), and are partly consistent with the phenotype. The embryonic expression of six of these genes CG1150; CG1153; CG15592; CG15598; CG1169; and CG15188) peaks in stages 13-16, while CG5189 is detected throughout embryogenesis and with a much broader tissue distribution than the others. CG15592, CG1169, and CG5188 are expressed in the embryonic tracheal system, CGl 5592 is expressed in the esophagus and foregut, and CG15598 is expressed in the esophagus and hindgut. Additional family members known to be expressed in late embryonic stages include CG1148, LD21503, SP558, and CG1157, consistent with a late embryonic lethal phase.

Expression of Osiris genes in later stages has also been observed. CG1153 shows two peaks of expression during metamorphosis in addition to one late in embryogenesis. The *Aedes aegypti* cDNA homolog to CG15596 is also expressed during metamorphosis. Also, the SP558 homolog in *Apis mellifera* was found in an adult brain cDNA library.

The Triplo-lethal locus has been mysterious since its discovery in 1972, primarily because point mutations and transposon insertional mutants could not be isolated. In 1979 Denell proposed three hypotheses to explain the peculiar genetic properties of Tpl. Subsequent work left the hypothesis of a cluster of related genes as the most likely. We tested this hypothesis by molecularly defining the limits of Tpl to approximately 334 kb, and examining the genomic sequence of that region. We found a large cluster of genes that are closely related and encode a novel family of transmembrane proteins with an extracellular domain containing a pair of cysteines and an intracellular domain containing endocytosis signalling motifs. With 23 members, this is one of the largest gene families in *Drosophila*. Of the 1437 sequence similarity groups reported at http://www.fruitfly.org/annot/similarity.html, only 26 groups have more than 23 members. Homologous genes have only been found in insects, and the function of this family is unknown in *Anopheles gambiae* or any other insect species. We predict that the orthologous families in *Anopheles* and other insects will also be dosage sensitive.

Reciprocal crosses between *D. melanogaster* carrying duplications and deficiencies of Tpl with *D. simulans, D. mauritiana* and *D. seychellia* have shown that Tpl is both triplo- and haplo-lethal to the interspecific hybrids of both sexes. These genes are also located in one of the longest regions of microsynteny between *D. melanogaster* and *A. gambiae*. Comparison of the sequences in the two species shows that in almost all cases the most closely related gene is the ortholog, rather than any of the paralogs. The low synonymous substitution rate appears to be due to strong codon bias, suggesting selection on expression level, and that the nonsynonymous substitution rate is lower than the synonymous rate suggests selection on function. These two observations, and the clustering of 20 of the 23 family members in 83DE are consistent with the Osiris cluster of proteins being the Triplo lethal locus.

The genetic data for Tpl led Denell to propose that the functions of the individual genes in the cluster are partially redundant; another possibility is a threshold effect such that duplication or deletion of multiple Osiris genes is needed in order to see the lethal dosage effects. Either of these possibilities could explain the inability of point mutants to complement duplications of the entire cluster. Subdivision of the cluster is now possible so these two hypotheses could be distinguished. Maintenance of the linkage relationships throughout evolution is reminiscent of the synteny maintained within the homoeotic gene families. It is possible that the tight linkage is maintained in response to selection—perhaps the genes are coordinately regulated or imprinted. In any case, the stability of the linkage arrangements and the sequences through long periods of time are unusual.

Without knowing the precise function of these proteins it is hard to know why this genetic region is so dosage sensitive. However the relative concentrations of membrane proteins can affect rates of association and assembly of complexes, leading to dosage sensitivity. The very high sequence conservation in the hydrophobic domain is intriguing. This region is somewhat long for a transmembrane domain, and it is not completely hydrophobic, showing a periodicity of prolines and glycines, as well as the lysines. These sequences are conserved in *Anopheles*, and suggests that this region has been under selection for more than just interacting with membrane lipids. This transmembrane domain likely interacts with other proteins—possibly each other in complexes, or with an intramembrane protease such as the rhomboid protein. Given that Tpl-trisomics are partially rescued by hyperoxia, the conserved pair of cysteines is also intriguing. It is possible that the extracellular cysteine pair responds to redox potential, and the intracellular tyrosines play a role in signalling. Finally, we wish to suggest that the extreme dosage sensitive lethality, the impossibility of rescuing duplications with point mutants, and the lack of homologs in other phyla suggest that this family of proteins would make an ideal target for genetic modifications or insecticide discovery in *Anopheles*, and other dipteran pests.

Of critical importance in the present invention is the fact that the Osiris family of genes are required for the survival of the insect and are present only in the insect family. The Osiris family cluster of genes occurs in a dosage sensitive region of the *Drosophila melanogaster* genome and represents an excellent target for insecticide discovery. It is worthwhile mentioning that this family is also present in *Anopheles gambiae* mosquitoes and several other insects of economic and public health importance.

The Osiris family of proteins is highly conserved. They all have a conserved sequence of amino acids unique to this class of proteins. These proteins present a novel target for insecticides due to their ubiquitous nature in insects yet minimal similarity to proteins of other phyla like vertebrates, plants, fungi, nematodes and bacteria. Insecticides targeted these proteins could become by far the most specific to insects. Also, due to the exposed nature of these proteins in the insects the insecticides do not even need to penetrate the cuticle in order to be effective.

Many insects evolve resistance to insecticides over time by amplifying or over expressing the target protein to compensate for the reduction in its activity caused by the insecticide. In this case, there are over 20 proteins in the Osiris family, so mutation of all 20 is statistically impossible.

Furthermore, resistance often evolves by a mechanism of over expressing the target protein to compensate for the reduction in its activity caused by the insecticide. Again, the presence of more than 20 protein targets makes this extremely unlikely, but in addition, over expression of these proteins by 50% or more is lethal, so over expression mediated resistance to insecticides is not possible.

One method for using the Osiris family is to test for compounds that inhibit the expression of or function of the proteins expressed by the sequences. Similar methods utilizing different genetic sequences are discussed in U.S. Patent Application No. 2002/0160934 by Broadus, et. al. and U.S. Pat. No. 6,468,770 to Keyes et. al., both of which are incorporated in their entirety by reference herein. Identification of a chemical compound that will bind to and inactivate the proteins of the Osiris family will yield an excellent insecticide. This method relies on the fact that these proteins are extremely well conserved across many species of insect, and are essential genes. Eliminating one copy of the cluster of Osiris1-20 is lethal, so finding a compound that will inactivate them completely (rather than reducing their activity by 50%, which is what the haplo-lethality is all about) should really kill them. The triplo-lethality offers a rationale that since resistance to insecticides often evolves by overexpressing, or amplifying the target gene, this won't happen with the Osiris genes, because overexpressing them by 50% is lethal. In addition, since there are no homologous genes in vertebrates, plants, fungi, bacteria, or any other animals besides insects, such insecticides will be specific and non-toxic.

Another method for controlling insect populations inherent in the present invention takes advantage of the haplo-lethality and triplo-lethality of the Osiris family. A tandem duplication of the Osiris 1-20 cluster (abbreviated Dup) contains two copies of each of the genes. A deletion of the entire cluster contains none (abbreviated Del). *D. melanogaster* flies have been modified to carry both: their genetic makeup is Dup/Del. Thus these flies have two copies of the cluster, and are normal. However, when they are mated to normal flies, half of the progeny will inherit the Dup from one parent and a normal chromosome (with one copy of the cluster) from the other. This is a total of three copies of the cluster, and these offspring will die. The other half of the progeny will inherit the Del from one parent and a normal chromosome from the other. This totals only one copy, and these offspring will also die.

Biological control can then be accomplished in the following manner: large numbers of Dup/Del insects can be raised in a laboratory, and then released into the wild. They will mate with the native population, but all the progeny of such matings will die. This wastes the egg capacity of the native females, and is damaging to the overall numbers of the population. Continued release can then limit population numbers. A similar method is used currently to control several species of insect including medflies, and screw-worms. These existing methods rely on exposing the lab-reared insects to X-rays as a means to sterilize them. The method of the present invention is advantageous in that X-ray exposure is not needed, as the success rate of mating Dup/Del insects, in some species at least, is likely very high.

What is claimed is:

1. A method for identifying a compound that inhibits the activity of a protein essential for insect viability, comprising:
   (a) expressing in a recombinant host a DNA molecule comprising a nucleotide sequence encoding an amino acid sequence of OSIRIS 7 (SEQ ID NO:7) to produce said protein essential for insect viability;
   (b) testing compounds suspected of having the ability to inhibit the activity of said protein essential for insect viability; and
   (c) identifying a compound tested in (b) that inhibits the activity of said protein essential for insect viability.

2. The method of claim 1 wherein said testing comprises placing said compound in contact with an insect.

3. The method of claim 2, wherein said identifying comprises killing an insect.

4. A method of testing a compound for insecticidal activity, comprising:
   (a) identifying a target compound that binds to a polypeptide sequence comprising an amino acid sequence of OSIRIS 7 (SEQ ID NO:7);
   (b) placing said target compound in contact with an insect; and
   (c) observing the reaction of said insect to said target compound.

5. The method of claim 4 wherein said target compound binds to an amino acid sequence of OSIRIS 7 (SEQ ID NO:7).

6. The method of claim 4 wherein said target compound binds to all polypeptide sequences comprising an amino acid sequence of OSIRIS 7 (SEQ ID NO:7).

7. A method of testing a compound for insecticidal activity, comprising:
   (a) identifying a target compound that binds to a polypeptide sequence comprising an amino acid sequence from the group consisting of OSIRIS 7 (SEQ ID NO:7), an ortholog thereof from *Anopheles* or a homolog thereof from *Drosophila pseudoobscura;*
   (b) placing said target compound in contact with an insect; and
   (c) observing the reaction of said insect to said target compound.

8. The method of claim 7, wherein said ortholog is syntenic with SEQ ID NO: 7.

9. The method of claim 7, wherein said homolog is syntenic with SEQ ID NO:7.

* * * * *

SEQUENCE LISTING

```
<160> NUMBER OF SEQ ID NOS: 1

<210> SEQ ID NO 1
<211> LENGTH: 202
<212> TYPE: PRT
<213> ORGANISM: Drosophila
<220> FEATURE:
<221> NAME/KEY: peptide
<222> LOCATION: (1)..(202)

<400> SEQUENCE: 1

Met Phe Arg Thr Phe Pro Leu Leu Cys Leu Leu Phe Leu Thr Ala Val
1               5                   10                  15

Arg Ser Glu Asn Cys Asp Gln Asp Ala Gly Ala Thr Leu Tyr Cys Arg
            20                  25                  30

Gly Glu Arg Ala Leu Arg Asn Val Leu Arg Asn Leu Asn Arg Ser Asp
        35                  40                  45

Lys Pro Leu Val Val Ile Arg Gly Leu Glu Ile Val Pro Leu Gln Asn
    50                  55                  60

Asn Ser Ile Ser Asp Glu Glu Pro Asp Gln Glu Gln Gly Leu Leu Asp
65                  70                  75                  80

Ser Leu Ser Phe Tyr Leu Arg Thr His Glu Ile Asn Val Lys Leu Ala
                85                  90                  95

Asp Leu Leu Glu Asp Glu Ser Gln Val Ser Glu Ala Arg Lys Lys Asp
            100                 105                 110

Lys Gly Gln Gly Met Leu Leu Ala Met Ala Leu Met Phe Gly Lys Met
        115                 120                 125

Met Ala Val Met Gly Leu Gly Gly Ile Ala Ala Leu Ala Met Lys Ala
    130                 135                 140

Leu Gly Val Ser Leu Val Ala Leu Met Met Ala Gly Met Leu Gly Leu
145                 150                 155                 160

Lys Thr Ala Ala Gln His Gly Gly Glu Ser Ser His Ser Ile Ser Tyr
                165                 170                 175

Val Thr Gly Glu Gly His His His Lys Arg Arg Arg Arg Ser Ser Gly
            180                 185                 190

Gln Gln Pro Leu Ala Tyr Arg Gly Trp Asp
        195                 200
```